US009714229B2

(12) United States Patent
Tanaka et al.

(10) Patent No.: US 9,714,229 B2
(45) Date of Patent: Jul. 25, 2017

(54) CRYSTAL OF TETRACYCLIC COMPOUND

(71) Applicant: Chugai Seiyaku Kabushiki Kaisha, Tokyo (JP)

(72) Inventors: Kota Tanaka, Tokyo (JP); Takamitsu Ueto, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/126,045

(22) PCT Filed: Apr. 24, 2015

(86) PCT No.: PCT/JP2015/062516
§ 371 (c)(1),
(2) Date: Sep. 14, 2016

(87) PCT Pub. No.: WO2015/163447
PCT Pub. Date: Oct. 29, 2015

(65) Prior Publication Data
US 2017/0081306 A1 Mar. 23, 2017

(30) Foreign Application Priority Data

Apr. 25, 2014 (JP) .................. 2014-092102

(51) Int. Cl.
*C07D 401/04* (2006.01)
*A61K 31/5377* (2006.01)

(52) U.S. Cl.
CPC ........ *C07D 401/04* (2013.01); *A61K 31/5377* (2013.01)

(58) Field of Classification Search
CPC .................................................. C07D 401/04
See application file for complete search history.

(56) References Cited

U.S. PATENT DOCUMENTS

| | | | |
|---|---|---|---|
| 5,721,267 A | 2/1998 | Broka | |
| 5,936,084 A | 8/1999 | Jirousek et al. | |
| 9,126,931 B2 | 9/2015 | Kinoshita et al. | |
| 2004/0076675 A1 | 4/2004 | Sugishita et al. | |
| 2005/0107364 A1 | 5/2005 | Hutchinson et al. | |
| 2007/0031907 A1 | 2/2007 | Pinna et al. | |
| 2007/0065516 A1 | 3/2007 | Sugishita et al. | |
| 2007/0099893 A1 | 5/2007 | Boyd et al. | |
| 2007/0249653 A1 | 10/2007 | Jagtap et al. | |
| 2008/0058320 A1 | 3/2008 | Herold et al. | |
| 2008/0090776 A1 | 4/2008 | Mano et al. | |
| 2008/0262021 A1 | 10/2008 | Capraro et al. | |
| 2009/0099193 A1 | 4/2009 | Mano et al. | |
| 2009/0221555 A1 | 9/2009 | Ahmed et al. | |
| 2010/0099658 A1 | 4/2010 | Kondoh et al. | |
| 2010/0240673 A1 | 9/2010 | Mano et al. | |
| 2011/0230545 A1 | 9/2011 | Mano et al. | |
| 2012/0083488 A1 | 4/2012 | Kinoshita et al. | |
| 2013/0143877 A1 | 6/2013 | Furumoto et al. | |
| 2013/0158095 A1 | 6/2013 | Mano et al. | |
| 2015/0184161 A1 | 7/2015 | Mano et al. | |
| 2015/0272958 A1 | 10/2015 | Kodama et al. | |

FOREIGN PATENT DOCUMENTS

| | | |
|---|---|---|
| CA | 2885733 A | 9/2015 |
| CN | 1902200 A | 1/2007 |
| EA | 001450 B1 | 4/2001 |
| EP | 1914240 B1 | 4/2008 |
| JP | 08-092090 A | 4/1996 |
| JP | 2008-280352 A | 11/2008 |
| JP | 2009-100783 A | 5/2009 |
| JP | 4588121 B1 | 9/2010 |
| JP | 4918630 B1 | 2/2012 |
| JP | 2012-126711 A | 7/2012 |
| RU | 2162089 C2 | 1/2001 |
| WO | WO 00/69856 A1 | 11/2000 |
| WO | WO 2004/080980 A1 | 9/2004 |
| WO | WO 2005/009389 A2 | 2/2005 |
| WO | WO 2005/097765 A1 | 10/2005 |
| WO | WO 2006/021884 A2 | 3/2006 |
| WO | WO 2007/023310 A2 | 3/2007 |
| WO | WO 2007/056497 A1 | 5/2007 |
| WO | WO 2007/130468 A2 | 11/2007 |
| WO | WO 2008/021369 A2 | 2/2008 |
| WO | WO 2008/051547 A1 | 5/2008 |
| WO | WO 2008/130951 A1 | 10/2008 |
| WO | WO 2009/008371 A1 | 1/2009 |
| WO | WO 2009/013126 A1 | 1/2009 |
| WO | WO 2009/073620 A2 | 6/2009 |
| WO | WO 2010/128324 A1 | 11/2010 |
| WO | WO 2010/142423 A2 | 12/2010 |
| WO | WO 2010/142685 A1 | 12/2010 |
| WO | WO 2014/050781 A1 | 4/2014 |

OTHER PUBLICATIONS

Bilsland et al., "Behavioral and Neurochemical Alterations in Mice Deficient in Anaplastic Lymphoma Kinase Suggest Therapeutic Potential for Psychiatric Indications," Neuropsychopharmacology, 2008, 33:685-700.
Byrn et al., "Pharmaceutical Solids: A Strategic Approach to Regulatory Considerations," Pharmaceutical Research, 1995, 12(7):945-954.
Soda et al., "Identification of the transforming EML4-ALK fusion gene in non-small-cell lung cancer," Nature, 2007, 448:561-566.
Ahlneck et al., "The molecular basis of moisture effects on the physical and chemical stability of drugs in the solid state," International Journal of Pharmaceutics, 1990, 62:87-95.
Bunz, F., "Chapter 1, The Genetic Basis of Cancer," Principles of Cancer Genetics, 2008, 1-47.
Caira, Mino R., "Crystalline Polymorphism of Organic Compounds," Topics in Current Chemistry, 1998, 198:163-208.
CAS RN 100863-39-6, STN Entry Date Mar. 15, 1986.
CAS RN 222318-66-3, STN Entry Date May 7, 1999.
CAS RN 24716-14-1, STN Entry Date Nov. 16, 1984.
CAS RN 36263-63-5, STN Entry Date Nov. 16, 1984.
CAS RN 4355-38-8, STN Entry Date Nov. 16, 1984.

(Continued)

*Primary Examiner* — Rebecca Anderson
(74) *Attorney, Agent, or Firm* — Foley & Lardner LLP

(57) ABSTRACT

The present invention relates to type II and type III crystals of 9-ethyl-6,6-dimethyl-8-(4-morpholin-4-yl-piperidin-1-yl)-11-oxo-6,11-dihydro-5H-benzo[b]carbazole-3-carbonitrile that is a pharmaceutically useful novel crystal.

6 Claims, 6 Drawing Sheets

(56) References Cited

OTHER PUBLICATIONS

CAS RN 6008-29-3, STN Entry Date Nov. 16, 1984.
CAS RN 61492-49-7, STN Entry Date Nov. 16, 1984.
CAS RN 74205-47-3, STN Entry Date Nov. 16, 1984.
CAS RN 89579-57-7, STN Entry Date Nov. 16, 1984.
CAS RN 93257-39-7, STN Entry Date Dec. 18, 1984.
Chen et al., "Oncogenic mutations of ALK kinase in neuroblastoma," Nature, Oct. 16, 2008, 455:971-974, and Methods page.
Cools et al., "Identification of Novel Fusion Partners of ALK, the Anaplastic Lymphoma Kinase, in Anaplastic Large-Cell Lymphoma and Inflammatory Myofibroblastic Tumor," Genes, Chromosomes & Cancer, 2002, 34:354-362.
Druker et al., "Section 1: Chronic Myelogenous Leukemia," Cancer: Principles & Practice of Oncology, 7th Edition (DeVita et al., Eds.), 2121. 2005.
Faderl et al., "Section 3: Myelodysplastic Syndromes," Cancer: Principles & Practice of Oncology, 7th Edition (DeVita et al., Eds.), 2144. 2005.
Fine et al., "Section 2: Neoplasms of the Central Nervous System," Cancer: Principles & Practice of Oncology, 7th Edition (DeVita et al., Eds.), 1834-1887. 2005.
Fischer et al., "A Ki-1(CD30)—Positive Human Cell Line (Karpas 299) Established From a High-Grade Non-Hodgkin's Lymphoma, Showing a 2;5 Translocation and Rearrangement of the T-Cell Receptor β-Chain Gene," Blood, Jul. 1988, 72(1):234-240.
Galkin et al., "Identification of NVP-TAE684, a potent, selective and efficacious inhibitor of NPM-ALK," PNAS, Jan. 2, 2007, 104(1):270-275 (and Corrections published in PNAS, Feb. 6, 2007, 104(6):2024-2025).
Garbett et al., "Extending Nature's Leads: The Anticancer Agent Ellipticine," Curr. Med. Chem.—Anti-Cancer Agents, 2004, 4:149-172.
George et al., "Activating mutations in ALK provide a therapeutic target in neuroblastoma,"Nature, 2008, 455:975-978.
Girouard et al., "Neurovascular coupling in the normal brain and in hypertension, stroke, and Alzheimer disease, " Journal of Applied Physiology, 2006, 100:328-335.
Glick et al., "Treatment with atypical antipsychotics: new indications and new populations," Journal of Psychiatric Research, 2001, 35:187-191.
Goel et al., "Mice transgenic for BRAF V600E demonstrate phenotype affecting melanocyte and neural lineages," Proceedings of the American Association for Cancer Research, Apr. 2006, 47:#273.
Goodman & Gilman's, Chemotherapy of Neoplastic Diseases, The Pharmacological Basis of Therapeutics, Brunton et al., Eds., 2008, 11th Ed., 853-908.
Griffin et al., "Recurrent Involvement of 2p23 in Inflammatory Myofibroblastic Tumors," Cancer Research, Jun. 15, 1999, 59:2776-2780.
Haleblian, John K., "Characterization of Habits and Crystalline Modification of Solids and Their Pharmaceutical Applications," Journal of Pharmaceutical Sciences, 1985, 64(8):1269-1288.
Hancock et al., "Characteristics and Significance of the Amorphous State in Pharmaceutical Systems," Journal of Pharmaceutical Sciences, 1997, 86(1):1-12.
Herbst et al., "ALK Gene Products in Anaplastic Large Cell Lymphomas and Hodgkin's Disease," Blood, Sep. 1, 1995, 86(5):1694-1700.
Huang et al., "An in vivo model to study human GSTP1 polymorphisms in osteosarcoma," Proceedings of the American Association for Cancer Research, Apr. 2006, 47:#271.
Hübinger et al., "CD30-mediated cell cycle arrest associated with induced expression of p21$^{CIP1/WAF1}$ in the anaplastic large cell lymphoma cell line Karpas 299," Oncogene, 2001, 20:590-598.
Jazii et al., "Identification of squamous cell carcinoma associated proteins by proteomics and loss of beta tropomyosin expression in esophageal cancer," World J. Gastroenterol., Nov. 28, 2006, 12(44):7104-7112.
Kinoshita et al., "Design and synthesis of a highly selective, orally active and potent anaplastic lymphoma kinase inhibitor (CH5424802)," Bioorganic & Medicinal Chemistry, 2012, 20(3):1271-1280.
Kirsch, Gilbert H., "Heterocyclic Analogues of Carbazole Alkaloids," Current Organic Chemistry, 2001, 5:507-518.
Kuppen et al., "Tumor structure and extracellular matrix as a possible barrier for therapeutic approaches using immune cells or adenoviruses in colorectal cancer," Histochem. Cell. Biol., 2001, 115:67-72.
Kuster, Bernhard, Ed., Kinase Inhibitors, Methods and Protocols, Methods in Molecular Biology, 2012, vol. 795, Chapter 1 by Fabbro et al., "Targeting Cancer with Small-Molecular-Weight Kinase Inhibitors.".
Kwak et al., "Anaplastic Lymphoma Kinase Inhibition in Non-Small-Cell Lung Cancer," The New England Journal of Medicine, Oct. 28, 2010, 363(18):1693-1703.
Lamant et al., "Establishment of a novel anaplastic large-cell lymphoma-cell line (COST) from a 'small-cell variant' of ALCL," Leukemia, 2004, 18:1693-1698.
Lissoni et al., "Biotherapy with the pineal hormone melatonin plus aloe and myrrh tincture in untreatable metastatic cancer patients as an essence therapy of cancer," Cancer Therapy, 2009, 7:397-401.
Luo et al., "Principles of Cancer Therapy: Oncogene and Non-oncogene Addiction," Cell, Mar. 6, 2009, 136:823-837.
Mosse et al., "Identification of ALK as a major familial neuroblastoma predisposition gene," Nature, Oct. 16, 2008, 455:930-935, and Methods page.
National Cancer Institute, http://www.cancer.gov/, "A to Z List of Cancers," downloaded May 29, 2014, 22 pages.
O'Brien et al., "Section 2: Chronic Lymphoid Leukemias," Cancer: Principles & Practice of Oncology, 7th Edition (DeVita et al., Eds.), 2133. 2005.
O'Brien et al., "Vascular cognitive impairment," The Lancet Neurology, Feb. 2003, 2:89-98.
Pao et al., "EGF receptor gene mutations are common in lung cancers from 'never smokers' and are associated with sensitivity of tumors to gefitinib and erlotinib," PNAS, Sep. 7, 2004, 101 36:13306-13311.
Piva et al., "Ablation of oncogenic ALK is a viable therapeutic approach for anaplastic large-cell lymphomas," Blood, Jan. 2006, 107(2):689-697.
Rosenwald et al., "t(1;2)(q21;p23) and t(2;3)(p23;q21): Two Novel Variant Translocations of the t(2:5)(p23;q35) in Anaplastic Large Cell Lymphoma," Blood, Jul. 1, 1999, 94(1):362-364.
Scheinberg et al,, "Section 2: Management of Acute Leukemias," Cancer: Principles & Practice of Oncology, 7th Edition (DeVita et al., Eds.), 2005, 2088, 2092.
Shah et at., "Current approaches in the treatment of Alzheimer's disease," Biomedicine & Pharmacotherapy, 2008, 62:199-207.
Shaw et al., "Targeting Anaplastic Lymphoma Kinase in Lung Cancer," Clinical Cancer Research, 2011, 17:2081-2086.
Shujuan, Wang, "The new insights on the diagnosis of malignant histiocytosis," Chinese Journal of Laboratory Medicine, Jan. 30, 2005, 28(1):14-16.
Silverman, Richard B., The Organic Chemistry of Drug Design and Drug Action, Second Ed., Elsevier Academic Press, Northwestern University, Evanston, Illinois, 2004, 29-31, table 2.2.
Soussi, Thierry, "p53 Antibodies in the Sera of Patients with Various Types of Cancer: A Review," Cancer Res., 2000, 60:1777-1788.
Stoica et al., "Identification of Anaplastic Lymphoma Kinase as a Receptor for the Growth Factor Pleiotrophin," J. Biol. Chem., May 18, 2001, 276(20:16772-16779.
Stoica et al., "Midkine Binds to Anaplastic Lymphoma Kinase (ALK) and Acts as a Growth Factor for Different Cell Types," J. Biol. Chem., Sep. 27, 2002, 277(39):35990-35998.
Wanner et al., "A convenient synthesis of 6-methylellipticine and 6-methylolivacine," Heterocycles, 1982, 19(12):2295-2300.
Wood et al., "Lack of the t(2;5) or Other Mutations Resulting in Expression of Anaplastic Lymphoma Kinase Catalytic Domain in CD30$^+$ Primary Cutaneous Lymphoproliferative Disorders and Hodgkin's Disease," Blood, Sep. 1, 1996, 88(5)1 765-1770.

(56) References Cited

OTHER PUBLICATIONS

Zhao et al., "The progress of the research on anaplastic lymphoma kinase genetic abnormality of anaplastic large cell lymphoma," Foreign Medical Sciences (Section of Blood Transfusion and Hematology), Oct. 15, 2004, 27(5):403-406.

CRYSTAL OF TETRACYCLIC COMPOUND

CROSS-REFERENCE TO RELATED APPLICATIONS

This application is a National Stage application of PCT/JP2015/062516, filed Apr. 24, 2015, which claims priority from Japanese application JP 2014-092102, filed Apr. 25, 2014.

TECHNICAL FIELD

The present invention relates to a novel crystal of a tetracyclic compound, or a salt or hydrate thereof.

BACKGROUND ART

Anaplastic Lymphoma Kinase (ALK) is one of the receptor tyrosine kinases belonging to the insulin receptor family (Non Patent Literature 1 and. Non Patent Literature 2). It is reported that genetic abnormalities of ALK cause production of abnormal kinases fused with other genes.

As diseases accompanied by the abnormalities of ALK, cancer and cancer metastasis (Non Patent Literature 1 and Patent Literature 1), depression, and cognitive dysfunction (Non Patent Literature 2), for example, are known, and effective therapeutic and preventive medicines these diseases are provided by providing an ALK inhibitor.

As a compound having an ALK inhibitory effect, a compound represented by formula (I) (compound name: 9-ethyl-6,6-dimethyl-8-(4-morpholin-4-yl-piperidin-1-yl)-11-oxo-6,11-dihydro-5H-benzo[b]carbazole-3-carbonitrile) and the like are known (Patent Literature 3, Patent Literature 4, and Patent Literature 5).

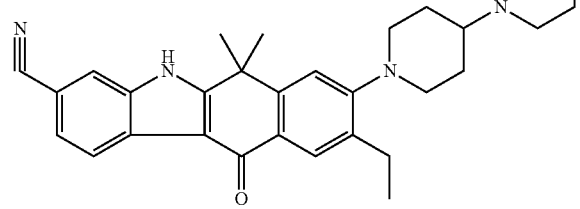

(1)

However, the crystal form of formula (I) has not been reported so far.

CITATION LIST

Patent Literatures

Patent Literature 1: Japanese Patent Laid-Open No. 2009-100783
Patent Literature 2: Japanese Patent Laid-Open No. 2008-280352
Patent Literature 3: Japanese Patent. No. 4588121
Patent Literature 4: Japanese Patent No, 4918630
Patent Literature 5: Japanese Patent Laid-Open No. 2012-126711

Non Patent Literatures

Non Patent Literature 1: Nature, vol. 448, p.p. 561-566, 2007

Non Patent Literature 2: Neuropsychopharmacology, vol. 33, p.p. 685-700, 2008

SUMMARY OF INVENTION

Technical Problem

As described above, the compound represented by formula (I) is known to have an ALK inhibitory activity, but a novel crystal that can be pharmaceutically useful has been desired.

Solution to Problem

As a result of diligent studies, the present inventors have found novel crystal forms (type II crystal and type III crystal) of the compound represented by formula (I).

That is, according to one aspect of the present invention, the following crystals (1) to (5) are provided:
(1) A crystal of a monohydrochloride of a compound represented by formula (I), having peaks at diffraction angles (2θ) of 9.2°±0.2°, 10.2°±0.2°, 16.2°±0.2°, 20.5°±0.2°, and 21.6°±0.2° in a powder X-ray diffraction pattern:

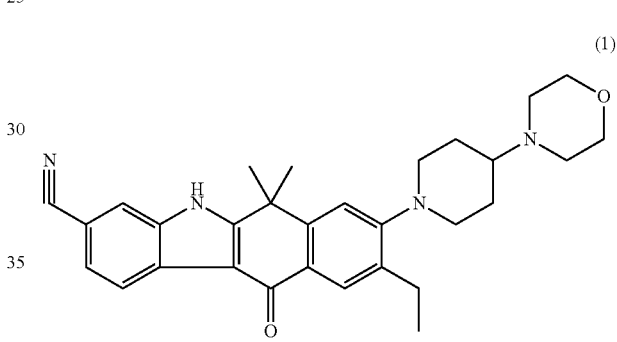

(1)

(2) The crystal according to (1), having peaks at diffraction angles (2θ) of 9.2°±0.2°, 10.2°±0.2°, 16.2°±0.2°, 17.5°±0.2°, 19.5°±0.2°, 20.5°±0.2°, 21.6°±0.2°, and 22.8°±0.2° in a powder X-ray diffraction pattern;
(3) The crystal according to (1) or (2), being a monohydrate crystal;
(4) A crystal of a monohydrochloride of a compound represented by formula (I), having peaks at diffraction angles (2θ) of 12.7°±0.2°, 143°±0.2°, 15.0°±0.2°, 18.5°+0.2°, and 25.7°±0.2° in a powder X-ray diffraction pattern; and
(5) The crystal according to (4), having peaks at diffraction angles (2θ) of 7.5°±0.2°, 12.7°±0.2°, 14.3°±0.2°, 15.0°±0.2°, 18.5°±0.2°, 20.3°±0.2°, 21.0°±0.2° and 25.7°±0.2° in a powder X-ray diffraction pattern.

Advantageous Effect of Invention

A novel crystal according to the present invention can be pharmaceutically useful.

DESCRIPTION OF EMBODIMENTS

A type II crystal of a monohydrochloride of the compound of formula (I) according to the present invention can be obtained by drying a type III crystal, which will be described below, at about 40° C. under reduced pressure.

Figure 1:
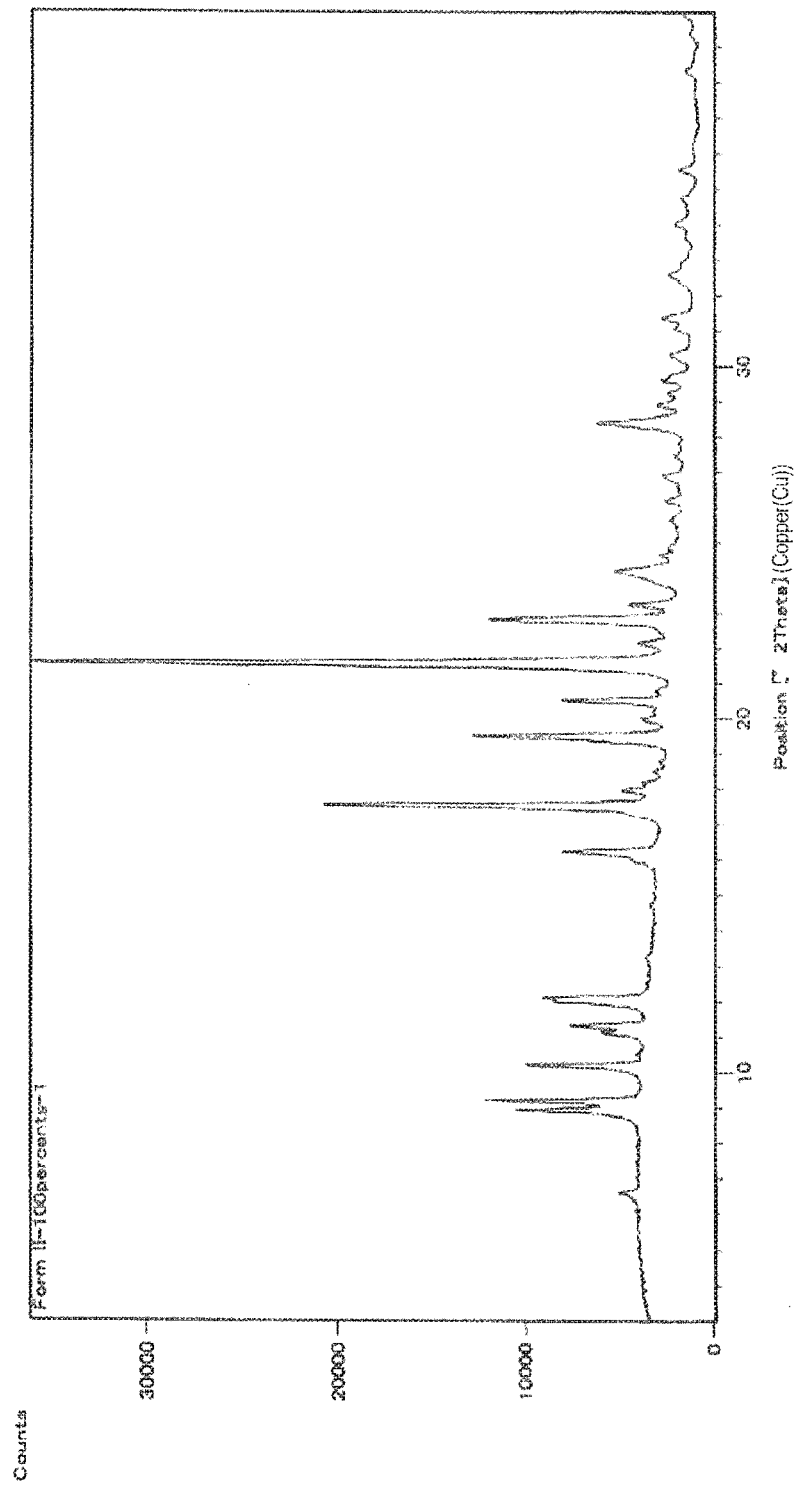
FIG. 1 is a graph of measurement results of powder X-ray diffraction for a type II crystal.

The type II crystal is characterized by having peaks at diffraction angles (2θ) of 9.2°, 10.2°, 16.2°, 20.5°, and 21.6°, more specifically, at diffraction angles (2θ) of 9.2°, 10.2°, 16.2°, 17.5°, 19.5°, 20.5°, 21.6°, and 22.8° in a powder X-ray diffraction pattern. An example of the measurement results of powder X-ray diffraction for the type II crystal is shown in FIG. 1, and an example of the peaks in the powder X-ray diffraction pattern is shown in Table 1.

TABLE 1

| Diffraction angle (2θ) | | |
| --- | --- | --- |
| 3.6 | 19.5 | 29.2 |
| 6.6 | 20.0 | 29.6 |
| 8.9 | 20.5 | 30.3 |
| 9.2 | 20.8 | 31.0 |
| 10.2 | 21.6 | 31.3 |
| 11.1 | 22.2 | 32.6 |
| 11.3 | 22.8 | 32.9 |
| 12.0 | 23.2 | 33.6 |
| 12.1 | 23.8 | 34.0 |
| 13.3 | 24.2 | 34.8 |
| 14.6 | 24.6 | 35.5 |
| 16.0 | 24.8 | 36.2 |
| 16.2 | 25.6 | 37.7 |
| 17.3 | 26.2 | 38.3 |
| 17.5 | 26.9 | 38.8 |
| 18.0 | 27.5 | 39.4 |
| 18.2 | 27.8 | 39.9 |
| 18.5 | 28.4 | |
| 18.8 | 28.9 | |

In one aspect of the present invention, the type II crystal is a monohydrate. Note that, the monohydrate is not specifically limited as long as it is a crystal that stably holds about one equivalent of water in an environment (such as temperature and relative humidity) in which pharmaceutical products are generally stored and used.

The type III crystal of the monohydrochloride of the compound of formula (I) according to the present invention can be obtained by adding dropwise a solution containing the compound of formula (I) to a mixture of ethanol and hydrochloric acid (containing one equivalent or more of hydrochloric acid with respect to the compound of formula (I)) while maintaining the temperature of the mixture at about 15° C.

Figure 2:
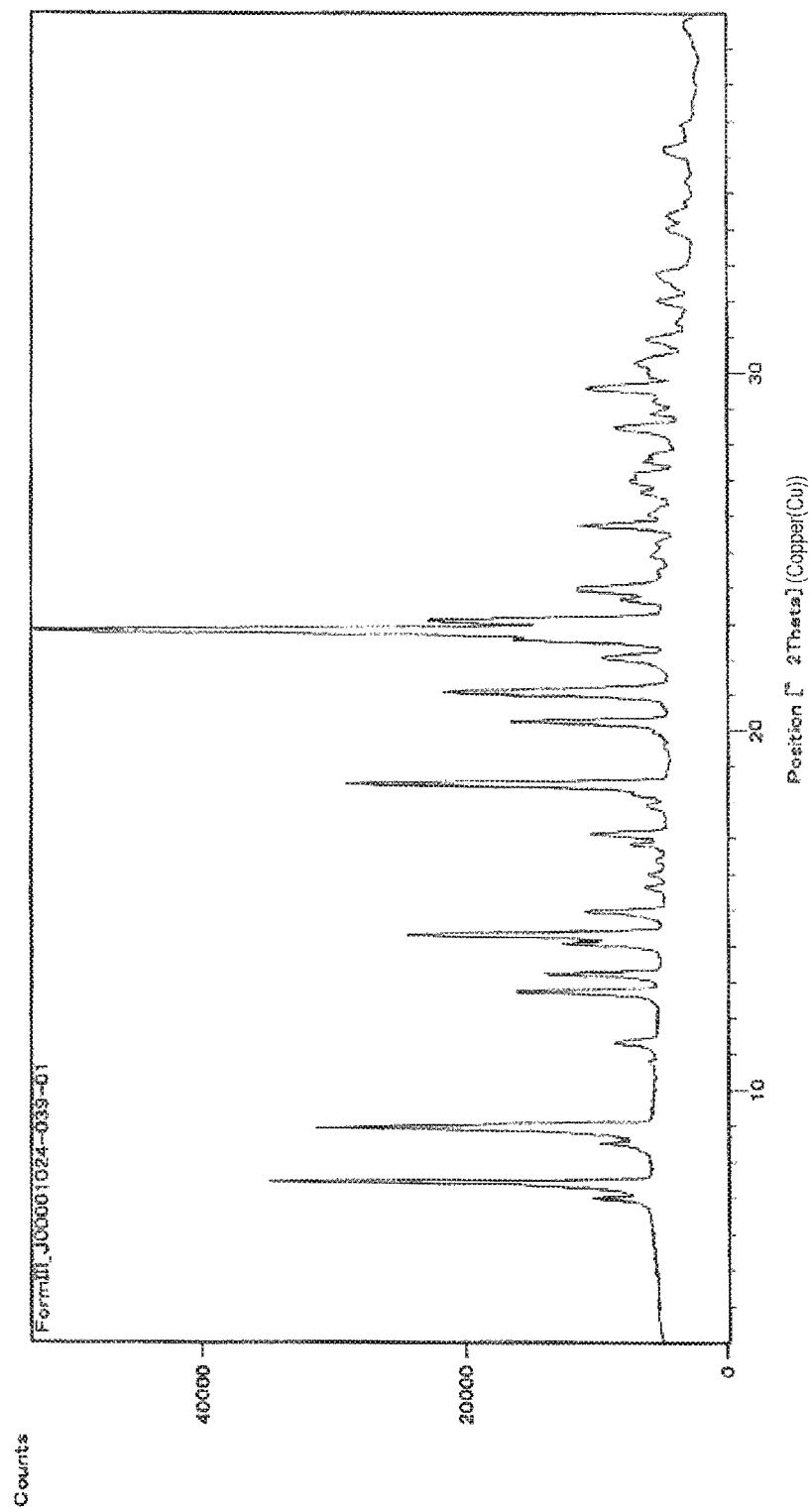
FIG. 2 is a graph of measurement results of powder X-ray diffraction for a type III crystal.

The type III crystal is characterized by having peaks in the powder X-ray diffraction pattern at diffraction angles (2θ) of 12.7°, 14.3°, 15.0°, 18.5° and 25.7°, more specifically, at diffraction angles (2θ) of 7.5°, 12.7°, 14.3°, 15.0°, 18.5°, 20.3°, 21.0° and 25.7°, An example of the measurement results of powder X-ray diffraction for the type III crystal is shown in FIG. 2, and an example of the peaks in the powder X-ray diffraction pattern is shown in Table 2.

TABLE 2

| Diffraction angle (2θ) | | |
| --- | --- | --- |
| 3.5 | 19.9 | 29.5 |
| 7.0 | 20.3 | 29.6 |
| 7.5 | 21.0 | 29.9 |
| 8.5 | 22.1 | 30.3 |
| 9.0 | 22.5 | 30.5 |
| 10.8 | 22.8 | 30.9 |
| 11.3 | 23.1 | 31.4 |
| 11.4 | 23.7 | 32.1 |
| 12.7 | 24.0 | 32.8 |
| 13.3 | 24.5 | 34.0 |
| 14.1 | 24.9 | 34.4 |
| 14.3 | 25.2 | 34.8 |
| 15.0 | 25.7 | 35.3 |
| 15.7 | 26.0 | 36.2 |
| 16.0 | 26.7 | 36.3 |
| 16.4 | 26.9 | 36.7 |
| 16.8 | 27.2 | 36.9 |
| 17.1 | 27.5 | 37.6 |
| 17.9 | 27.7 | 38.2 |
| 18.2 | 28.5 | |
| 18.5 | 28.8 | |
| 19.6 | 29.1 | |

In the present invention, an analysis by the powder X-ray diffraction can be performed, for example, in accordance with a conventional method such as "powder X-ray diffraction measurement method" described in the Japanese Pharmacopoeia (15th revision) Further, according to the Japanese Pharmacopoeia, the same crystal forms usually have the same diffraction angles 2θ within the range of ±0.2 degree. Accordingly, the present invention includes not only crystals having diffraction angles of the peaks in the powder X-ray diffraction that completely agree with each other but also crystals having diffraction angles of the peaks that agree with each other within a margin of error of about ±0.2 degree.

An example of the measurement conditions in the powder X-ray diffraction analysis is shown below.

Measuring apparatus: X'Pert-Pro MPD (manufactured by PANalytical BV)
Anticathode: Cu
Tube voltage: 45 kV
Tube current: 40 mA
Step width: 0.02
Scan axis: 2θ
Sampling time per step: 43 seconds
Scan range: 3 to 40°

The water content in crystals can be measured by a conventional method, such as using a dynamic vapor sorption isotherm instrument or the Karl Fischer's method.

An example of the measurement conditions when using the dynamic vapor sorption isotherm instrument is shown below.

Dynamic vapor sorption isotherm instrument: DVS-1 (Surface Measurement Systems)
Temperature: Constant temperature of about 25° C.
Atmospheric gas: Dry nitrogen
Flow rate of atmospheric gas: 200 sccm (ml/min)
Minimum waiting time: 10 min
Maximum waiting time: 1200 min An example of the measurement conditions in the method for measuring the water content using a Karl Fischer Analyzer is shown below.

Analysis method: Coulometric titration
KF analyzer: Trace moisture analyzer, type KF-100 (manufactured by Mitsubishi Chemical Corporation)

Anode liquid: AQUAMICRON AX (manufactured by Mitsubishi Chemical Corporation)

Cathode liquid: AQUAMICRON CXU (manufactured by Mitsubshi Chemical Corporation)

Figure 3:
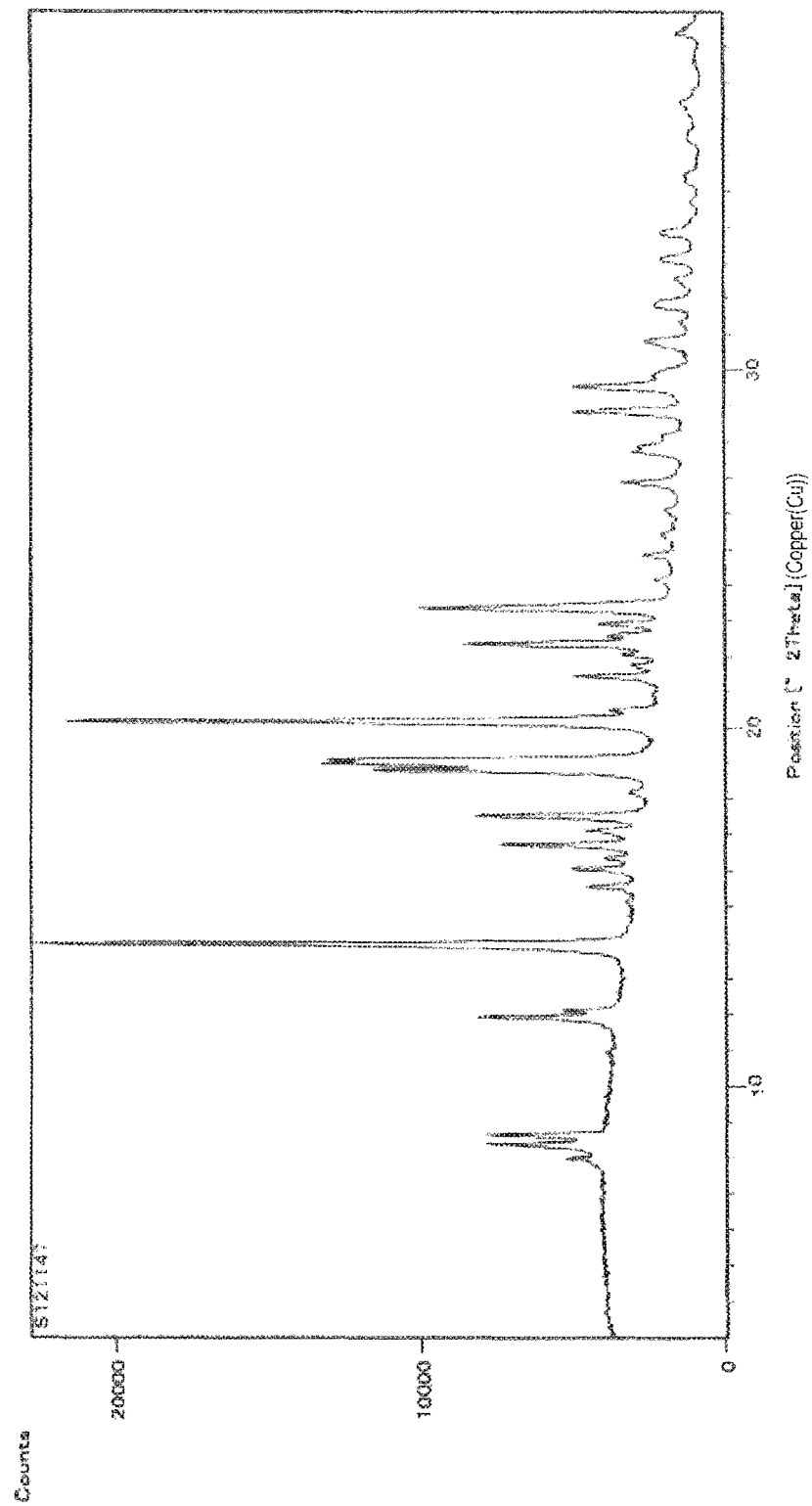
FIG. 3 is a graph of measurement results of powder X-ray diffraction for a type I crystal.

The present inventors have further specified a crystal of the above-described compound of formula (I) (hereinafter, referred to as type I crystal) that is different from the type II crystal and the type III crystal. The type I crystal can be obtained by adding dropwise a solution containing the compound of formula (I) to a mixture of ethanol and hydrochloric acid. (containing one molar equivalent or more of hydrochloric acid with respect to the compound of formula (I)) while maintaining the temperature of the mixture at about 35° C. or more. The type I crystal is characterized by having peaks in the powder X-ray diffraction pattern at diffraction angles (2θ) of 8.4°, 14.0°, 16.7°, 18.8°, and 23.3°. An example of the measurement results of powder X-ray diffraction for the type I crystal is shown in FIG. 3, and an example of the peaks in the powder X-ray diffraction pattern is shown in Table 3.

TABLE 3

| Diffraction angle (2θ) | | |
|---|---|---|
| 3.5 | 20.2 | 28.8 |
| 8.0 | 20.5 | 29.5 |
| 8.4 | 21.0 | 29.9 |
| 8.7 | 21.5 | 30.8 |
| 11.0 | 21.8 | 31.3 |
| 11.9 | 22.1 | 31.8 |
| 12.1 | 22.3 | 31.9 |
| 14.0 | 22.6 | 32.6 |
| 15.1 | 22.9 | 33.1 |
| 15.6 | 23.3 | 33.2 |
| 16.1 | 24.1 | 33.8 |
| 16.4 | 24.8 | 34.7 |
| 16.7 | 25.4 | 35.3 |
| 17.1 | 25.7 | 35.5 |
| 17.5 | 26.1 | 36.4 |
| 18.2 | 26.9 | 36.6 |
| 18.8 | 27.7 | 37.5 |
| 19.0 | 27.9 | 38.8 |
| 19.1 | 28.2 | 39.4 |

The compound represented by formula (I) and its hydrochloride can be produced in accordance with the methods described in Patent Literatures 3 to 5, but not limited to them.

EXAMPLES

Hereinafter, suitable examples of the present invention will be described further in detail. However, the present invention is not limited to these examples.

Example 1

Type I crystal of monohydrochloride of 9-ethyl-6,6-dimethyl-8-(4-morpholin-4-yl-piperidin-1-yl)-11-oxo-6,11-dihydro-5H-benzo[b]carbazole-3-carbonitrile 400 g of 9-ethyl-6,6-dimethyl-8-(4-morpholin-4-yl-piperidin-1-yl)-11-oxo-6,11-dihydro-5H-benzo[b]carbazole-3-carbonitrile was dissolved in a mixture of 4.8 L of methyl ethyl ketone, 1.44 L of acetic acid, and 1.68 L of distilled water at room temperature, and this solution was added dropwise to a mixture of 12 L of ethanol and 0.8 L of 2 N hydrochloric acid at 60° C. A precipitated solid was collected by filtration and was washed with 2 L of ethanol followed by drying, to obtain 357 g of the type I crystal of the monohydrochloride of the titled compound.

Example 2

Type III crystal of monohydrochloride of 9-ethyl-6,6-dimethyl-8-(4-morpholin-4-yl-piperidin-1-yl)-11-oxo-6,11-dihydro-5H-benzo[b]carbazole-3-carbonitrile 9-Ethyl-6,6-dimethyl-8-(4-morpholin-4-yl-piperidin-1-yl)-11-oxo-6,11-dihydro-5H-benzo[b]carbazole-3-carbonitrile (9.00 g) was dissolved in a mixture of methyl ethyl ketone (90 ml), distilled water (31.5 ml), and acetic acid (27.0 ml). This solution was added dropwise to a mixture of ethanol (90 ml) and 2N hydrochloric acid (18.00 ml) that was stirred at 15° C. while maintaining the temperature of the mixture at 15° C. Subsequently, after washing with a mixture of methyl, ethyl ketone (18.00 ml), distilled water (6.30 ml), and acetic acid (5.40 ml), the mixture was stirred at 15° C. A precipitated solid, was collected by filtration, to obtain the type III crystal of the monohydrochloride of the titled compound.

Example 3

Type II crystal of monohydrochloride of 9-ethyl-6,6-dimethyl-8-(4-morpholin-4-yl-piperidin-1-yl)-11-oxo-6,11-dihydro-5H-benzo[b]carbazole-3-carbonitrile The III crystal obtained in Example 2 was washed with ethanol (90 ml), followed by drying at 40° C. for about 16 hours under reduced pressure, to obtain the type II crystal of the monohydrochloride of the titled compound.

Example 4

Type II crystal of monohydrochloride of 9-ethyl-6,6-dimethyl-8-(4-morpholin-4-yl-piperidin-1-yl)-11-oxo-6,11-dihydro-5H-benzo[b]carbazole-3-carbonitrile 9-ethyl-6,6-dimethyl-8-(4-morpholin-4-yl-piperidin-1-yl)-11-oxo-6,11-dihydro-5H-benzo[b]carbazole-3-carbonitrile (4.00 g) was added to a mixture of methyl ethyl ketone (40 ml), distilled water (14 ml), and acetic acid (12 ml) to be dissolved therein at 35° C. This solution was added dropwise to a mixture of ethanol (40 ml) and 2N hydrochloric acid (8.00 ml) (stirred at 15° C.) while maintaining the temperature of the mixture at 15° C. To this mixture, a mixture of methyl ethyl ketone (8.00 ml), distilled water (2.80 ml), and acetic acid (2.40 ml) was further added dropwise while maintaining the temperature of the mixture at 15° C. Subsequently, the mixture was stirred at 15° C. A precipitated solid was collected by filtration and was washed with ethanol (40 ml), followed by drying at 40° C. under reduced pressure, to obtain the type II crystal of the monohydrochioride of the titled compound (2.4805 g).

Example 5

Type III crystal of monohydrochloride of 9-ethyl-6,6-dimethyl-8-(4-morpholin-4-yl-piperidin-1-yl)-11-oxo-6,11-dihydro-5H-benzo[b]carbazole-3-carbonitrile 9-ethyl-6,6-dimethyl-8-(4-morpholin-4-yl-piperidin-1-yl)-11-oxo-6,11-dihydro-5H-benzo[b]carbazole-3-carbonitril (4.00 g) was added to a mixture of methyl ethyl ketone (40 ml), distilled water (14 ml), and acetic acid (12 ml) to be dissolved therein at 35° C. This solution was added dropwise to a mixture of ethanol (40 ml) and 2N hydrochloric acid (8.00 ml) (stirred at 15° C.) while maintaining the temperature of the mixture at 15° C. A mixture of methyl ethyl ketone (8.00 ml), distilled water (2.80 ml), and acetic acid (2.40 ml) was added dropwise thereto while maintaining the temperature of the mixture at 15° C. Subsequently, the mixture was stirred at 15° C. A precipitated solid was collected by filtration, to obtain the type III crystal of the monohydrochloride of the titled compound (7.8435 g).

[Experimental Example 1] Powder X-Ray Diffraction Analysis

For the type I, type II, and type III crystals of a monohydrochloride of 9-ethyl-6,6-dimethyl-8-(4-morpholin-4-yl-piperidin-1-yl)-11-oxo-6,11-dihydro-5H-benzo[b]carbazole-3-carbonitrile, the powder X-ray diffraction was measured under the following conditions. The measurement results for the type II crystal, the type III crystal, and the type I crystal are shown in FIGS. 1, 2, and 3.
  Measuring apparatus: X'Pert-Pro MPD (manufactured by PANalytical HV)
  Anticathode: Cu
  Tube voltage: 45 kV
  Tube current: 40 mA
  Step width: 0.02
  Scan axis: 20
  Sampling time per: 43 seconds
  Scan range: 3 to 40°

Figure 4:
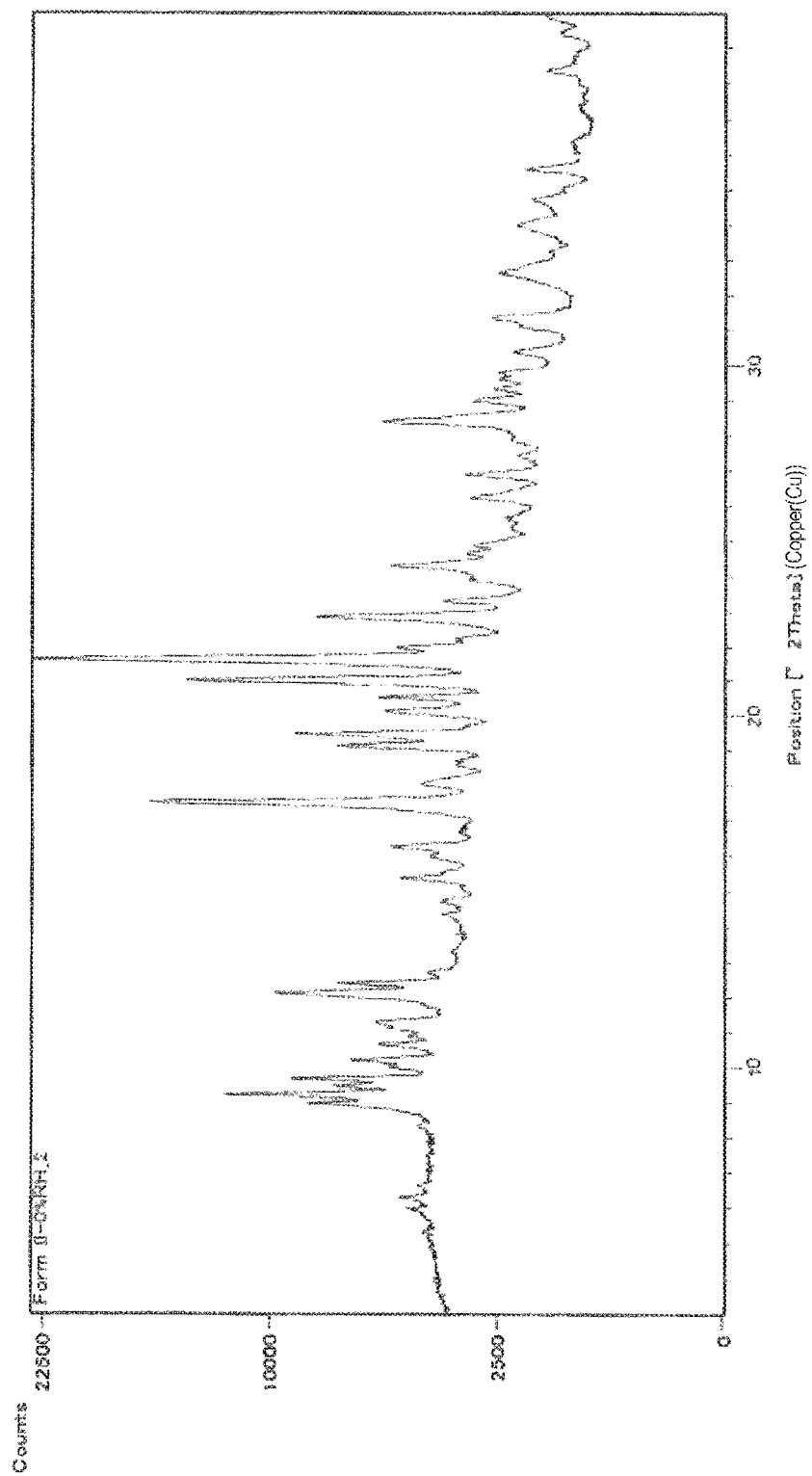
FIG. 4 is a graph of measurement results of powder X-ray diffraction for the type II crystal after being stored at low humidity.

[Experimental Example 2] Investigation on Transformation of Crystal form of Type II Crystal Due to Humidity In order to investigate the transformation of the crystal form of the type II crystal of the monohydrochloride of 9-ethyl-6,6-dimethyl-8-(4-morpholin-4-yl-piperidin-1-yl)-11-oxo-6,11-dihydro-5H-benzo[b]carbazole-3-carbonitrile due to humidity, samples were placed in the following humidity conditions, and changes in crystal form were investigated using the powder X-ray diffraction.
Test Conditions 1 (Investigation on Transformation of Crystal form of Type II Crystal at Low Humidity)
  Amount of sample: About 17 mq
  Temperature: Constant temperature of about 25° C.
  Atmospheric gas: Dry nitrogen
  Flow rate of atmospheric gas: 200 sccm (ml/min)
  Mass change rate: 0.002 dm/dt
  Relative humidity: Samples were placed at a relative humidity of 0% RH
  Minimum waiting time: 10 min
  Maximum waiting time: 1200 min.
Test Conditions 2 (Iinvestigation on Transformation of Crystal Form of Type II Crystal at High Humidity)
  Amount of sample: About 16 mg
  Temperature: Constant temperature of about 25° C.
  Atmospheric s: Dry nitrogen
  Flow rate of atmospheric gas: 200 sccm (ml/min)
  Mass change rate: 0.002 dm/dt (%/min)
  Relative humidity: Samples were placed at a relative humidity of 70% RH
  Minimum waiting time: 10 min
  Maximum waiting time: 1200 min From the results of the powder X-ray diffraction, it was revealed that transformation into another crystal form was caused when the type II crystal was stored at low humidity (FIG. 4). When the type II crystal was allowed to stand in the air, the crystal form of the type II crystal rapidly returned to the original crystal form within one hour. It is inferred from this that the type II crystal dehydrates to be a anhydrate in low humidity environment (at a relative humidity of 15% RH or less). Further, it was revealed that the type II crystal contained water of crystallization.

Figure 5:
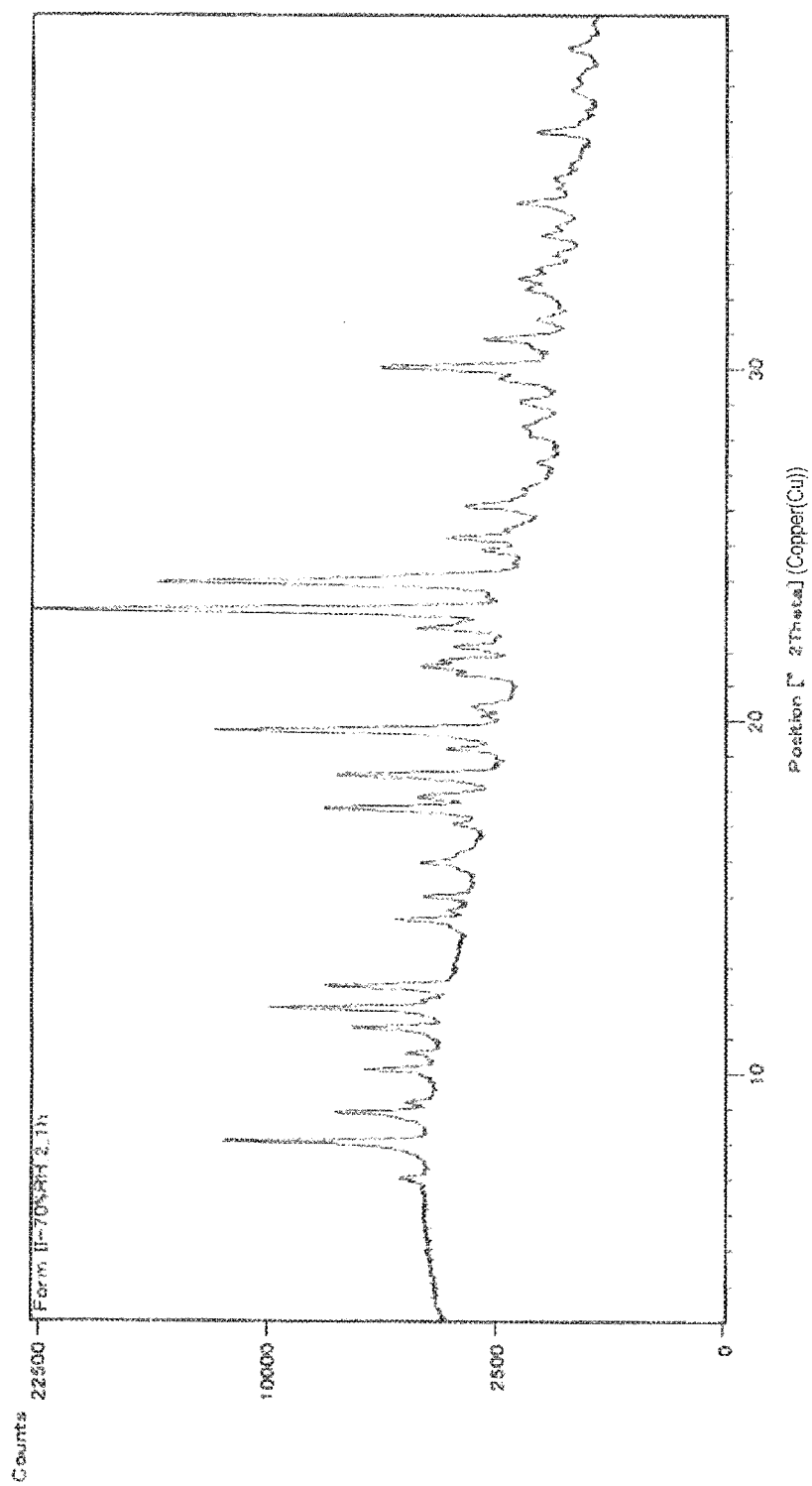
FIG. 5 is a graph of measurement results of powder X-ray diffraction for the type II crystal after being stored at a relative humidity of 70% RH.

When stored at 70% RH, the type II crystal showed a powder X-ray diffraction pattern (FIG. 5) different from the powder X-ray diffraction pattern of the type II crystal. It was revealed from this that transformation into another crystal form was caused when the type II crystal was stored at high humidity. As the crystal was allowed to stand in the air, and the powder X-ray diffraction was measured over time, the crystal form returned to the original form, type II crystal, in the measurement after 4 hours. It is inferred from this that the type II crystal absorbs moisture in high humidity environment (at a relative humidity of 65 RH or more), to transform into another crystal form containing water of crystallization.

Figure 6:
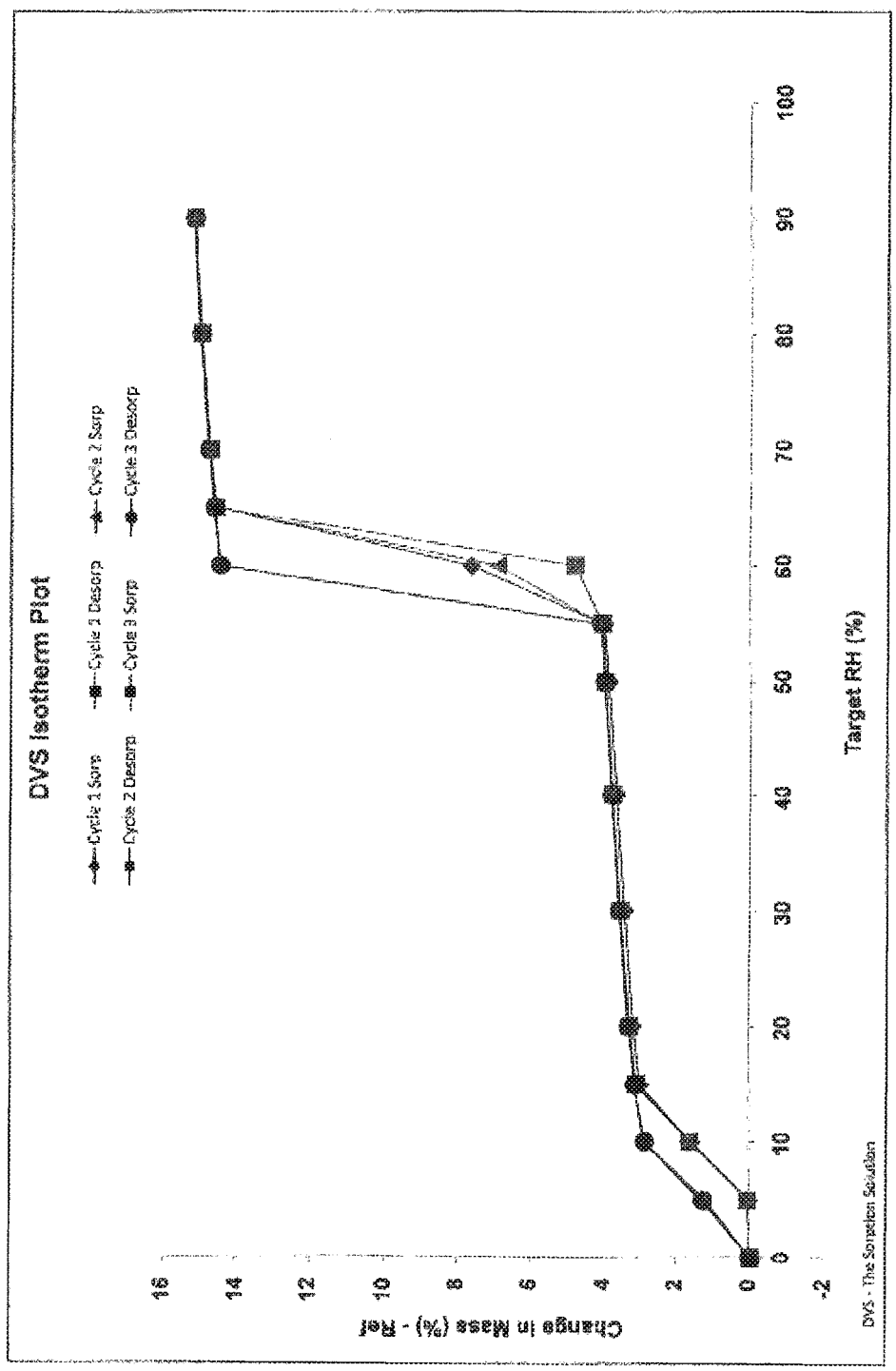
FIG. 6 is a graph of measurement results of weight change rate (%) for the type II crystal in a temperature environment at a relative humidity ranging from 0% RH to 90% RH.

[Experimental Example 3] Measurement of Vapor Sorption Isotherm of Type II Crystal For the type II crystal of the monohydrochloride of 9-ethyl-6,6-dimethyl-8-(4-morpholin-4-yl-piperidin-1-yl)-11-oxo-6,11-dihydro-5H-benzo[b]carbazole-3-carbonitrile (about 5 mg), the vapor sorption isotherm was measured using a dynamic vapor sorption isotherm instrument: DVS-1 (Surface Measurement Systems) under the following conditions.
Test Conditions
  Temperature: Constant temperature of about 25° C.
  Atmospheric gas: Dry nitrogen
  Flow rate of atmospheric gas: 200 sccm (ml/min)
  Minimum waiting time: 10 min
  Maximum waiting time: 1200 min
  Mass change rate: 0.002 dm/dt (% min), where the mass change rate was 0.001 dm/dt (% min) at 5, 10, 15, 55, 60, and 65% RH.
  Relative humidity: Relative humidity was varied to 0, 5, 10, 15, 20, 30, 40, 50, 55, 60, 65, 70, 80, 90, 80, 70, 65, 60, 55, 50, 40, 30, 20, 15, 10, 5, and 0% RR in this order. Such variation was regarded as one cycle, and three cycles were carried out. The measurement results are shown in FIG. 6.
The weight change rate (%) of the type II crystal, when the temperature environment was varied from a relative humidity of 0% RH to 90% RH at about 25° C., was 3.7% in the range of a relative humidity from 0% RH to 15% RH, 0.05% in the range of a relative humidity from 15% RH to 55% RH, 11% in the range of a relative humidity from 55% RH to 65% RH, and 0.04% in the range of a relative humidity from 65% RH to 90% RH.

Assuming that the type II crystal was a monohydrochloride monohydrate of the compound of formula (I), the molecular weight would be 537.0928. From the molecular weight and mass change rate (%), it is inferred that the type II crystal is a monohydrochloride monohydrate and is dehydrated when it is stored in an atmosphere of 0% RH, so as to be transformed into a monohydrochloride. Further, it is inferred that the type II crystal absorbs moisture in high humidity environment with a humidity of 65% RH or more and is transformed into a monohydrochloride tetrahydrate.

The invention claimed is:

1. A crystal of a monohydrochloride of a compound represented by formula (I), having peaks at diffraction angles (2θ) of 9.2°±0.2°, 10.2°±0.2°, 16.2°±0.2°, 20.5°±0.2°, and 21.6°±0.2° in a powder X-ray diffraction pattern:

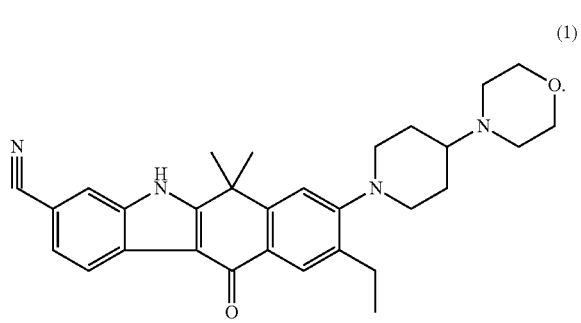 [SMILES: CCc1cc2c(cc1N1CCC(N3CCOCC3)CC1)C(C)(C)c1[nH]c3cc(C#N)ccc3c1C2=O]

2. The crystal according to claim 1, having peaks at diffraction angles (2θ) of 9.2°±0.2°, 10.2°±0.2°, 16.2°±0.2°, 17.5°±0.2°, 19.5°±0.2°, 20.5°±0.2°, 21.6°±0.2°, and 22.8°±0.2° in a powder X-ray diffraction pattern.

3. The crystal according to claim 1, being a monohydrate crystal.

4. A crystal of a monohydrochloride of a compound represented by formula (I), having peaks at diffraction angles (2θ) of 12.7°±0.2°, 14.3°±0.2°, 15.0°±0.2°, 18.5°±0.2°, and 25.7°±0.2° in a powder X-ray diffraction pattern

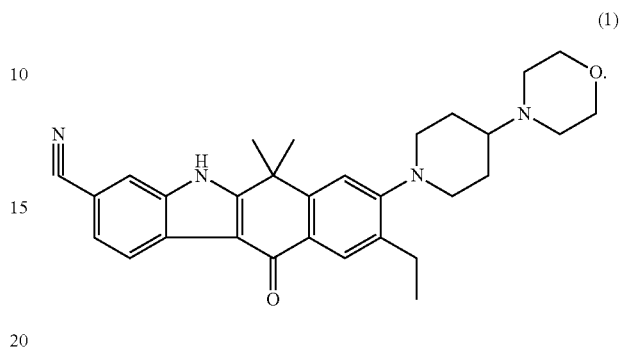

5. The crystal according to claim 4, having peaks at diffraction angles (2θ) of 7.5°±0.2°, 12.7°±0.2°, 14.3°±0.2°, 15.0°±0.2°, 18.5°±0.2°, 20.3°±0.2°, 21.0°±0.2°, and 25.7°±0.2° in a powder X-ray diffraction pattern.

6. The crystal according to claim 2, being a monohydrate crystal.

* * * * *